United States Patent
Moseley

(10) Patent No.: US 11,849,975 B1
(45) Date of Patent: Dec. 26, 2023

(54) METHODS FOR SINGLE INCISION ANTERIOR AND POSTERIOR SPINAL FUSION PROCEDURE

(71) Applicant: Spinal Simplicity, LLC, Overland Park, KS (US)

(72) Inventor: Todd Moseley, Olathe, KS (US)

(73) Assignee: Spinal Simplicity, LLC, Overland Park, KS (US)

( * ) Notice: Subject to any disclaimer, the term of this patent is extended or adjusted under 35 U.S.C. 154(b) by 0 days.

(21) Appl. No.: 17/983,805

(22) Filed: Nov. 9, 2022

(51) Int. Cl.
  *A61B 17/70* (2006.01)
  *A61B 17/17* (2006.01)
  *A61F 2/44* (2006.01)
  *A61B 17/02* (2006.01)

(52) U.S. Cl.
  CPC .......... *A61B 17/70* (2013.01); *A61B 17/1757* (2013.01); *A61F 2/4455* (2013.01); *A61B 2017/0256* (2013.01)

(58) Field of Classification Search
  CPC ....... A61B 17/7065–7068; A61B 17/88; A61F 2/4405
  See application file for complete search history.

(56) References Cited

U.S. PATENT DOCUMENTS

| | | | |
|---|---|---|---|
| 8,945,184 B2 | 2/2015 | Hess et al. | |
| 9,314,276 B2 | 4/2016 | Hess et al. | |
| 9,757,164 B2 | 9/2017 | Hess et al. | |
| 9,861,399 B2 | 1/2018 | Rogers et al. | |
| 9,907,581 B2 | 3/2018 | Hess et al. | |
| 10,420,591 B2 | 9/2019 | Snell et al. | |
| 11,298,161 B2 | 4/2022 | Snell et al. | |
| 11,311,388 B2 | 4/2022 | Frock et al. | |
| 11,311,389 B2 | 4/2022 | Frock et al. | |
| 11,534,310 B2 | 12/2022 | Frock et al. | |
| 2001/0005796 A1* | 6/2001 | Zdeblick | A61F 2/4611 623/17.11 |
| 2002/0040243 A1* | 4/2002 | Attali | A61F 2/4601 623/17.16 |
| 2008/0208344 A1* | 8/2008 | Kilpela | A61F 2/442 623/17.11 |
| 2009/0292316 A1* | 11/2009 | Hess | A61B 17/7065 606/279 |

(Continued)

OTHER PUBLICATIONS

Slover, Jeff et al.; U.S. Appl. No. 17/716,833, filed Apr. 8, 2022.

*Primary Examiner* — Eduardo C Robert
*Assistant Examiner* — Michelle C Eckman
(74) *Attorney, Agent, or Firm* — ERISE IP, P.A.

(57) ABSTRACT

Methods for anterior fusion and posterior fusion spinal procedures are disclosed. The spinal procedure may be a minimally invasive procedure. An incision may be made on a back of a patient to provide percutaneous lateral access to a spine of the patient. The access point of Kambin's triangle may be used to reach an intervertebral disc space. Through the incision and with an anterior trajectory, an interbody cage may be inserted into the intervertebral disc space. Thereafter, through the same incision and with a posterior trajectory, a spinal fusion implant may be inserted into an interspinous process space or an interlaminar space. The procedure may be performed through a single incision. The same surgical instrumentation may be used for both the anterior fusion and the posterior fusion procedures.

20 Claims, 9 Drawing Sheets

(56) References Cited

U.S. PATENT DOCUMENTS

| | | | |
|---|---|---|---|
| 2010/0057130 A1* | 3/2010 | Yue | A61B 17/7065 606/279 |
| 2011/0230965 A1* | 9/2011 | Schell | A61B 17/7064 606/86 A |
| 2012/0041272 A1* | 2/2012 | Dietze, Jr. | A61B 17/025 600/231 |
| 2014/0074170 A1* | 3/2014 | Mertens | A61F 2/4611 606/279 |
| 2015/0032163 A1* | 1/2015 | Abdou | A61B 17/7065 606/279 |
| 2016/0045326 A1* | 2/2016 | Hansen | A61F 2/447 623/17.16 |
| 2016/0262805 A1* | 9/2016 | Rogers | A61B 17/7068 |
| 2020/0306055 A1* | 10/2020 | Greenhalgh | A61B 17/7064 |

* cited by examiner

METHODS FOR SINGLE INCISION ANTERIOR AND POSTERIOR SPINAL FUSION PROCEDURE

TECHNICAL FIELD

Embodiments of the present disclosure generally relate to a system and method for spinal procedures. More specifically, embodiments of the present disclosure relate to systems and methods for anterior and posterior spinal fusion procedures through a lateral incision.

RELATED ART

The spine consists of a column of twenty-four vertebrae that extend from the skull to the hips. Discs of soft tissue are disposed between adjacent vertebrae. In addition, the spine encloses and protects the spinal cord, defining a bony channel around the spinal cord, called the spinal canal. There is normally a space between the spinal cord and the borders of the spinal canal so that the spinal cord and the nerves associated therewith are not pinched.

Over time, the ligaments and bone that surround the spinal canal can thicken and harden, resulting in a narrowing of the spinal canal and compression of the spinal cord or nerve roots. This condition is called spinal stenosis, which results in pain and numbness in the back and legs, weakness, and/or a loss of balance. These symptoms often increase after walking or standing for a period of time.

There are a number of non-surgical treatments for spinal stenosis. These include non-steroidal anti-inflammatory drugs to reduce the swelling and pain, and corticosteroid injections to reduce swelling and treat acute pain. While some patients may experience relief from symptoms of spinal stenosis with such treatments, many do not, and thus turn to surgical treatment. The most common surgical procedure for treating spinal stenosis is decompressive laminectomy, which involves removal of parts of the vertebrae. The goal of the procedure is to relieve pressure on the spinal cord and nerves by increasing the area of the spinal canal.

Interspinous process decompression (IPD) is a less invasive surgical procedure for treating spinal stenosis. With IPD surgery, there is no removal of bone or soft tissue; instead, an implant or spacer device is positioned behind the spinal cord or nerves and between the interspinous processes that protrude from the vertebrae in the lower back.

Examples of particularly useful interspinous process implant and fusion devices are disclosed in commonly assigned U.S. Pat. Nos. 9,861,399, 8,945,184; 9,314,276, 9,907,581, 9,757,164, 11,311,388, 11,311,389, and U.S. Patent Application No. 2022/0175548, the disclosures of which are all incorporated herein by reference in their entirety.

SUMMARY

Embodiments of the present disclosure address the above-identified need by providing systems and methods for an anterior interbody and posterior fusion procedure, including via a single incision. A minimally invasive incision may be made to provide percutaneous lateral access to a patient's spine. Kambin's triangle may be used as an access point for accessing an intervertebral disc space via an anterior trajectory. An interbody cage may be inserted into the intervertebral space to promote fusion between adjacent vertebrae. The interbody cage may comprise extendable wings configured to engage with the adjacent vertebrae to promote rotational stability of the vertebrae. A spinal implant may be inserted through the same incision, via a posterior trajectory, and into an interspinous or interlaminar space to fuse the spinous processes or the laminae.

In some aspects, the techniques described herein relate to a method for a single incision anterior fusion and posterior fusion spinal procedure, the method including: providing instructions for performing the single incision anterior fusion and posterior fusion spinal procedure, the instructions including: make a minimally invasive incision on a patient to provide percutaneous lateral access to a spine of the patient; advance a guidewire through the minimally invasive incision and into an intervertebral disc space located between a first vertebra and a second vertebra of the spine; advance at least one dilator through the minimally invasive incision and over the guidewire to dilate the intervertebral disc space; advance at least one sleeve through the minimally invasive incision and over the at least one dilator; insert, via an anterior trajectory and through an access point defined by Kambin's triangle, an interbody cage into the intervertebral disc space; reposition the guidewire to access a target space between the first vertebra and the second vertebra; and insert, via a posterior trajectory, a spinal fusion implant through the minimally invasive incision and to the target space for stabilization at the target space.

In some aspects, the techniques described herein relate to a method, wherein the target space is an interspinous process space, and wherein the spinal fusion implant is configured to fuse a first spinous process of the first vertebra with a second spinous process of the second vertebra.

In some aspects, the techniques described herein relate to a method, wherein the instructions further include: deploy a first wing and a second wing of the spinal fusion implant, wherein the first wing is configured to engage with the first spinous process, and the second wing is configured to engage with the second spinous process; and deploy a first wing and a second wing of the interbody cage, wherein the first wing and the second wing of the interbody cage are configured to engage with the first vertebra and the second vertebra.

In some aspects, the techniques described herein relate to a method, wherein the instructions further include: distract the first spinous process and the second spinous process with a bone tap.

In some aspects, the techniques described herein relate to a method, wherein the target space is an interlaminar space of the patient, and wherein the spinal fusion implant is configured to fuse a first lamina to a second lamina.

In some aspects, the techniques described herein relate to a method, wherein the interbody cage includes external threads, the external threads including a pair of opposing flats, and wherein the pair of opposing flats are configured to aid in insertion of the interbody cage and provide rotational stability.

In some aspects, the techniques described herein relate to a method, wherein the instructions further include: add bone graft material to at least one of the interbody cage or the spinal fusion implant to promote bony fusion between the first vertebra and the second vertebra.

In some aspects, the techniques described herein relate to a method, wherein the instructions further include: prior to inserting the interbody cage into the intervertebral disc space, remove at least a portion of an intervertebral disc disposed in the intervertebral disc space; and replace the portion of the intervertebral disc with bone graft.

In some aspects, the techniques described herein relate to a method, wherein the single incision anterior fusion and posterior fusion procedure is performed in a lumbar spine of the patient.

In some aspects, the techniques described herein relate to a method, wherein the minimally invasive incision includes a length of less than about 2.6 centimeters.

In some aspects, the techniques described herein relate to a method for a single incision anterior fusion and posterior fusion spinal procedure, the method including: providing instructions for performing the single incision anterior fusion and posterior fusion spinal procedure, the instructions including: make a minimally invasive incision onto a lateral side of a patient; access an intervertebral disc space of a spine of the patient using a guidewire; insert, via an anterior trajectory and through Kambin's triangle, an interbody cage through the minimally invasive incision and into the intervertebral disc space, wherein the interbody cage includes a first wing and a second wing, wherein the first wing and the second wing are deployable and configured to provide rotational stability between vertebrae adjacent to the intervertebral disc space; access an interlaminar space of the spine of the patient using the guidewire; advance at least one dilator through the minimally invasive incision and over the guidewire to dilate the interlaminar space; advance at least one sleeve over the at least one dilator; remove the guidewire from the patient; and insert, via a posterior trajectory, a spinal implant into the interlaminar space.

In some aspects, the techniques described herein relate to a method, wherein the instructions further include: distract the interlaminar space of the spine using a bone tap inserted through the minimally invasive incision and over the guidewire.

In some aspects, the techniques described herein relate to a method, wherein the interbody cage includes external threads, the external threads including a pair of opposing flats, and wherein the pair of opposing flats are configured to aid in insertion of the interbody cage.

In some aspects, the techniques described herein relate to a method, wherein the instructions further include: remove at least a portion of an intervertebral disc prior to inserting the interbody cage.

In some aspects, the techniques described herein relate to a method, wherein the instructions further include: remove at least a portion of a facet using a facet rasp to enhance access to the interlaminar space.

In some aspects, the techniques described herein relate to a method, wherein the minimally invasive incision is made on the patient lying in a prone position, and wherein the minimally invasive incision is configured to provide percutaneous lateral access to the spine of the patient.

In some aspects, the techniques described herein relate to a system for a single incision anterior and posterior spinal fusion procedure, the system including: a guidewire configured for insertion into an incision, wherein the incision is a minimally invasive incision configured to provide percutaneous lateral access to a spine of a patient; at least one dilator configured to be advanced over the guidewire to dilate the patient; at least one sleeve configured to be advanced over the at least one dilator; an interbody cage configured to be inserted through the incision and the at least one sleeve and into an intervertebral disc space, wherein the interbody cage is configured to be inserted through Kambin's triangle and via an anterior trajectory; and a spinal implant configured to be inserted through the incision and across an interspinous process space of the patient, wherein the spinal implant is configured to be inserted via a posterior trajectory.

In some aspects, the techniques described herein relate to a system, wherein the interbody cage includes: a first wing and a second wing, wherein the first wing and the second wing are configured to engage with a superior vertebra and an inferior vertebra of the intervertebral disc space.

In some aspects, the techniques described herein relate to a system, wherein the interbody cage includes external threads, the external threads including a pair of opposing flats, and wherein the pair of opposing flats are configured to aid in insertion of the interbody cage.

In some aspects, the techniques described herein relate to a system, wherein at least one of the interbody cage or the spinal implant is configured to hold bone graft material.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the current present disclosure will be apparent from the following detailed description of the embodiments and the accompanying drawing figures.

BRIEF DESCRIPTION OF THE FIGURES

Embodiments of the present disclosure are described in detail below with reference to the attached drawing figures, wherein.

Figure 1:
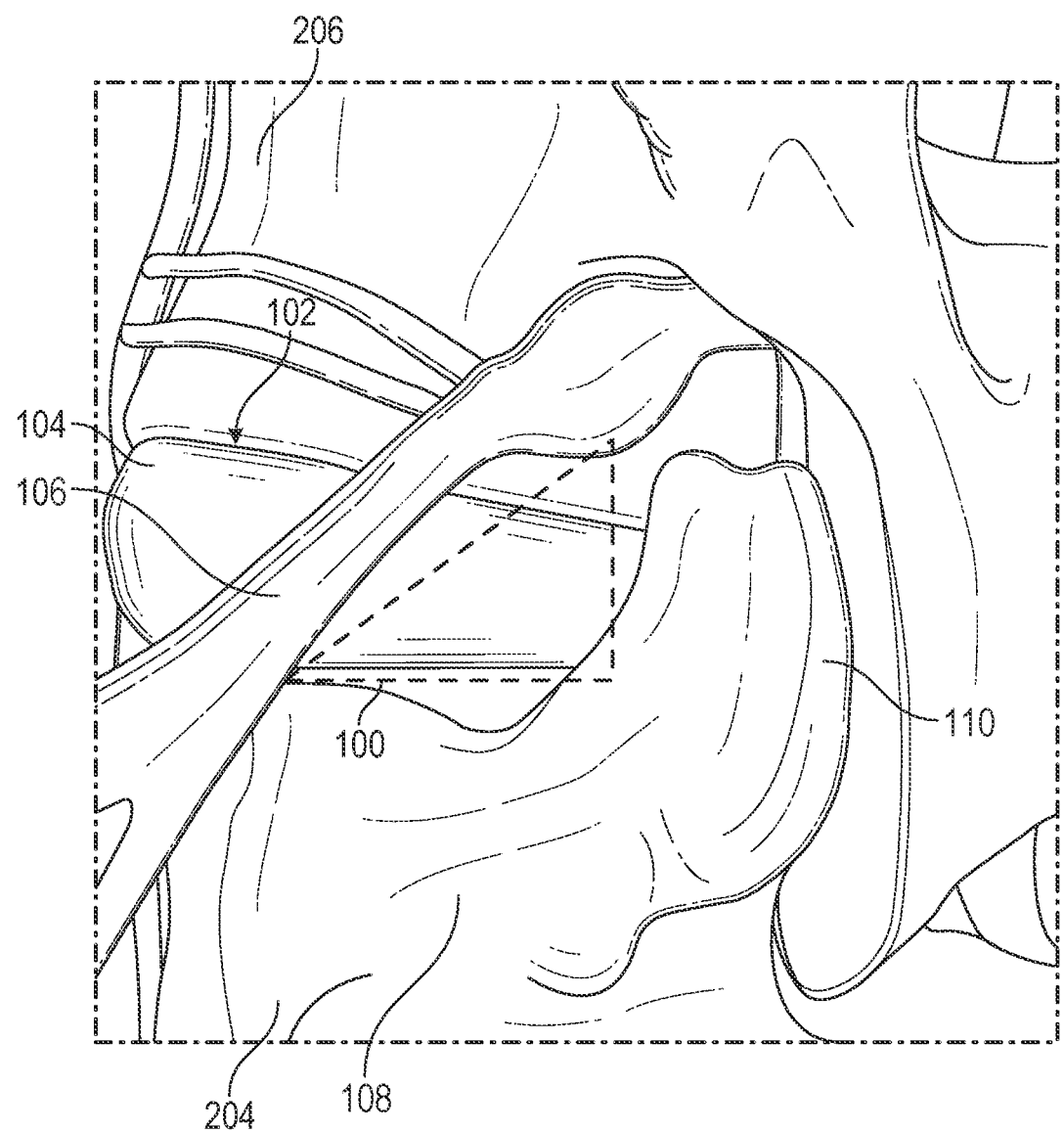
FIG. 1 illustrates an access point defined by Kambin's triangle for access to an intervertebral disc space of a spine.

The drawing figures do not limit the present disclosure to the specific embodiments disclosed and described herein. The drawings are not necessarily to scale, emphasis instead being placed upon clearly illustrating the principles of the present disclosure.

DETAILED DESCRIPTION

The subject matter of the present disclosure is described in detail below to meet statutory requirements; however, the description itself is not intended to limit the scope of claims.

Rather, the claimed subject matter might be embodied in other ways to include different steps or combinations of steps similar to the ones described in this document, in conjunction with other present or future technologies. Minor variations from the description below will be understood by one skilled in the art and are intended to be captured within the scope of the claims. Terms should not be interpreted as implying any particular ordering of various steps described unless the order of individual steps is explicitly described.

The following detailed description of embodiments of the present disclosure references the accompanying drawings that illustrate specific embodiments in which the present disclosure can be practiced. The embodiments are intended to describe aspects of the present disclosure in sufficient detail to enable those skilled in the art to practice the present disclosure. Other embodiments can be utilized and changes can be made without departing from the scope of the present disclosure. The following detailed description is, therefore, not to be taken in a limiting sense. The scope of embodiments of the present disclosure is defined only by the appended claims, along with the full scope of equivalents to which such claims are entitled.

In this description, references to "one embodiment," "an embodiment," or "embodiments" mean that the feature or features being referred to are included in at least one embodiment of the technology. Separate reference to "one embodiment" "an embodiment", or "embodiments" in this description do not necessarily refer to the same embodiment and are also not mutually exclusive unless so stated and/or except as will be readily apparent to those skilled in the art from the description. For example, a feature, structure, or act described in one embodiment may also be included in other embodiments but is not necessarily included. Thus, the technology can include a variety of combinations and/or integrations of the embodiments described herein.

Embodiments are generally directed to systems and methods for an anterior and posterior spinal fusion procedure, including via a single incision. The single incision may be a minimally invasive incision and made on a patient lying posteriorly or laterally to provide percutaneous lateral access to the patient's spine. A minimally invasive incision may comprise an incision of less than about two inches, in contrast to traditional open surgeries having five to six inch incisions. Minimally invasive surgeries allow for muscle to be distracted as opposed to cut away as in open surgeries, which allows for quicker recoveries. Minimally invasive surgeries further reduce blood loss, hospital stay, and recovery time as compared to open surgeries. The anterior interbody fusion may be performed through the access point of Kambin's triangle. One or more interbody cages may be inserted into an intervertebral disc space between adjacent vertebrae to restore spacing therebetween. Through the same incision, a posterior spinal fusion procedure may be performed. The posterior fusion may be performed with a posterior trajectory and may involve the insertion of an implant device inserted into an interspinous process space of the adjacent vertebrae. In some embodiments, the implant device is inserted into an interlaminar space. Performing both the anterior interbody and the posterior interspinous procedures through the same incision can reduce recovery time, hospital stay, post-operative pain, blood loss, and scarring when compared to making multiple minimally invasive incisions or performing an open surgery. Furthermore, the same preparatory instrumentation, such as guidewires, dilators, and sleeves, may be used for both the anterior procedure and the posterior procedure.

Kambin's Triangle

FIG. 1 illustrates Kambin's triangle 100, which will be useful in understanding embodiments described herein. Kambin's triangle 100 is an anatomical corridor in the lumbar spine that provides a safe access point for percutaneous access to an intervertebral disc space 102, in which an intervertebral disc 104 is located, that does not contain critical vascular and neural structures. Therefore, accessing the intervertebral disc space 102 via the access point of Kambin's triangle 100 can reduce potential surgical complications when performing spinal procedures.

Kambin's triangle 100 may be accessed by making a lateral incision on the back of a patient and via an anterior trajectory. Kambin's triangle 100 is large enough for minimally invasive procedures to be performed therein. The hypotenuse of Kambin's triangle 100 is formed by an exiting root nerve 106; the base of Kambin's triangle 100 is formed by the superior endplate vertebra 108; and the height of Kambin's triangle 100 is the traversing root nerve 110. During surgery, guidewires, sleeves, dilators, interbody cages, and other surgical instrumentation may traverse through Kambin's triangle 100 to access intervertebral disc space 102. Kambin's triangle 100 may be accessed using a transforaminal lumbar interbody fusion approach, which is discussed in further detail below.

Anterior Interbody Fusion and Interbody Cage

Figure 2A:
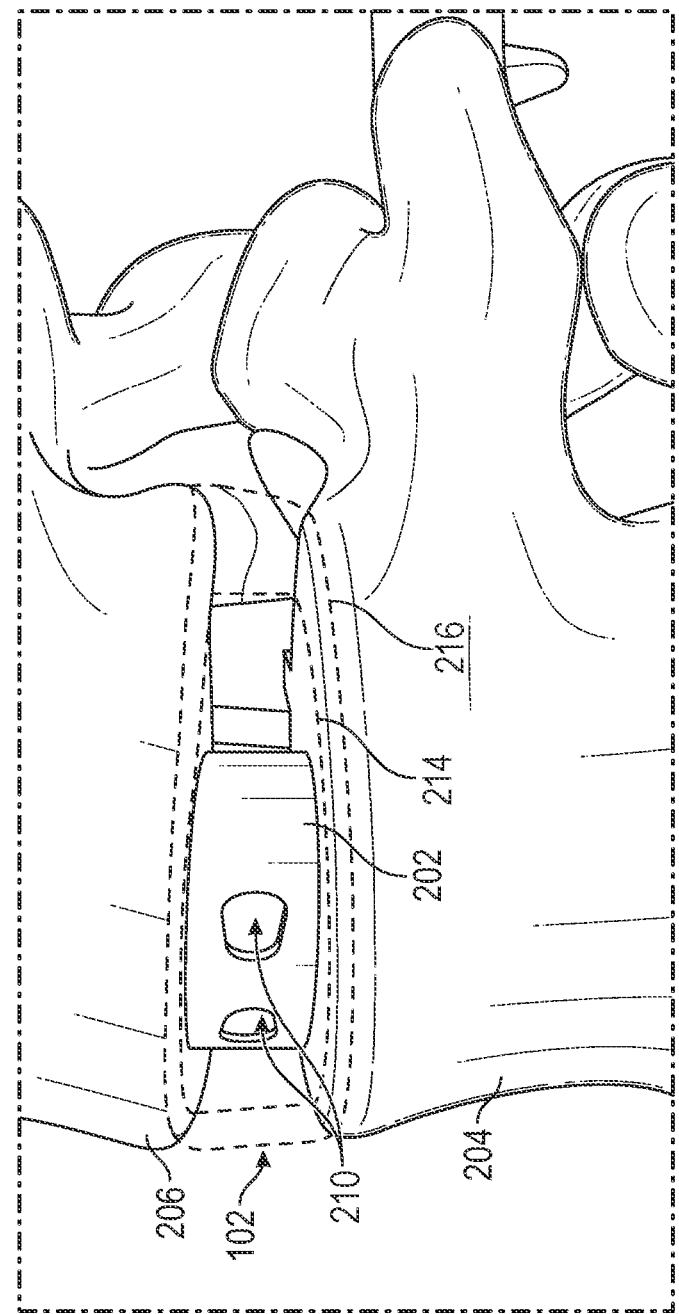
FIG. 2A illustrates a first view of an interbody cage inserted into the intervertebral disc space for some embodiments.
Figure 2B:
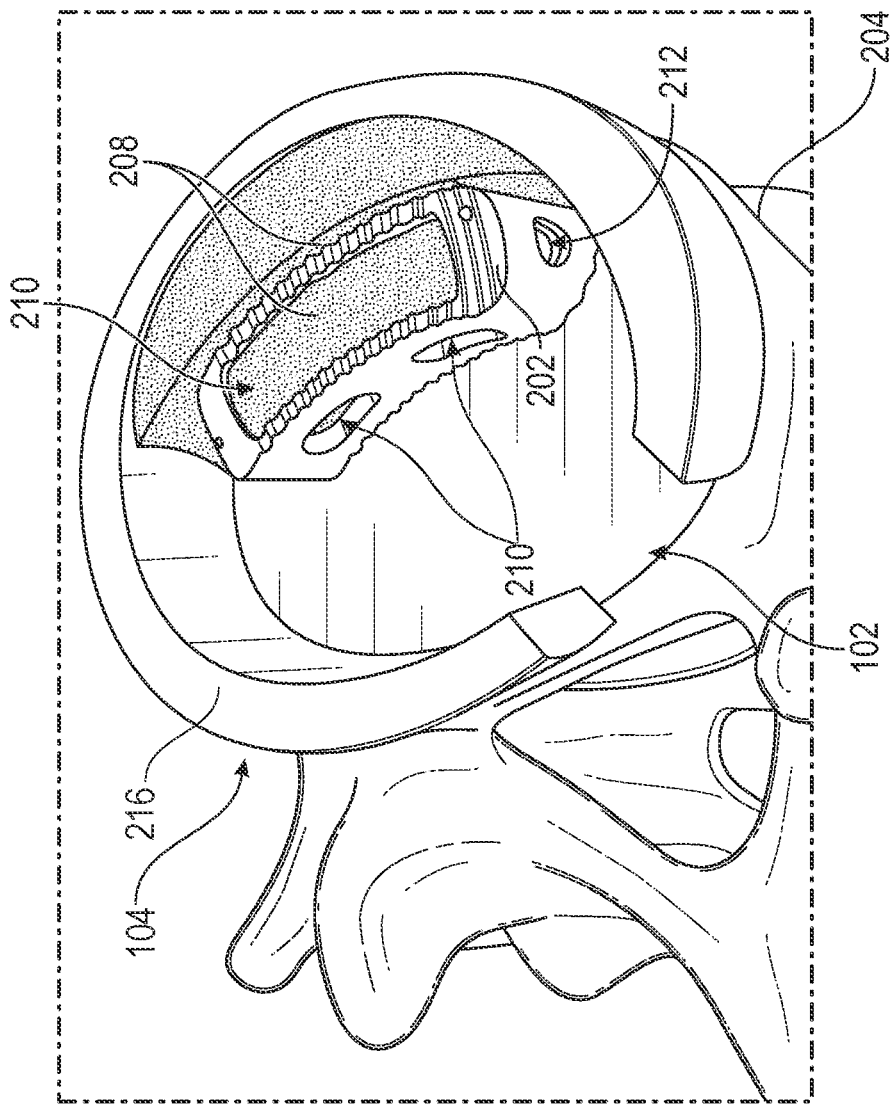
FIG. 2B illustrates a second view of the interbody cage inserted into the intervertebral disc space for some embodiments.

FIGS. 2A and 2B illustrate an interbody cage 202 inserted into intervertebral disc space 102 as a result of an anterior interbody fusion procedure for some embodiments. FIG. 2A illustrates a perspective view of interbody cage 202 in intervertebral disc space 102, between a first vertebra 204 (also referred to as an inferior vertebra) and a second vertebra 206 (also referred to as a superior vertebra). FIG. 2B illustrates a top down view of interbody cage 202 inserted into intervertebral disc space 102 with second vertebra 206 omitted for clarity of illustration. Vertebrae 204, 206 may be vertebrae of the lumbar spine. For example, first vertebra 204 may be the L3 vertebra, and second vertebra 206 may be the L2 vertebra. In some embodiments, the procedure is performed at the L5-S1 level of the spine. As used herein, the term "interbody cage" includes an intervertebral spacer device that is configured to be inserted between vertebrae in the spine.

An anterior interbody fusion procedure may be performed to correct degenerative spinal conditions, such as degenerative disc disease or spinal stenosis. One or more interbody cages 202 may be inserted in intervertebral disc space 102 to increase and/or restore the amount of space between vertebrae 204, 206. Intervertebral disc space 102 may be accessed via Kambin's triangle 100 as described above.

The interbody cage 202 may be cylindrical, trapezoidal, rectangular, disc-shaped, or various other shapes without departing from the scope hereof. In some embodiments, interbody cage 202 comprises a tapered end. Interbody cage 202 may be configured to hold bone graft 208. Threading and/or teeth may be disposed on an outer surface of interbody cage 202 to aid in fusion and stability of the vertebrae 204, 206. The interbody cage 202 may be formed from titanium, titanium alloy, polyether ether ketone (PEEK), or another polymer or bioabsorbable material, or any combination thereof.

In some embodiments, interbody cage 202 is filled with bone graft 208 to promote bony fusion over time such that first vertebra 204 and second vertebra 206 fuse together to form a single bony part. Bone graft 208 may be artificial or may be an autograft taken from the patient, such as from the iliac crest. Alternatively, or additionally, bone graft 208 may be an allograft. In some embodiments, interbody cage 202 comprises at least one opening 210 in which the surgeon may add bone graft 208. In some embodiments, bone graft 208 may be added externally to interbody cage 202. In some embodiments, interbody cage 202 comprises a bore 212 for advancing interbody cage 202 along a guidewire.

The anterior interbody fusion procedure may be performed as follows. The anterior interbody fusion procedure may be performed under anterior-posterior (AP) fluoroscopy to view the positioning and insertion of interbody cage 202 and the various instrumentation used during the procedure. A patient may be placed in a prone position on a frame to decrease the lordosis of the spine and avoid compression of the abdomen. In some embodiments, the patient is placed in a lateral decubitus position. Using a laterally minimally invasive surgical (MIS) approach, an incision may be made to provide percutaneous lateral access to the spine. The incision may be made by first identifying a midline of the spinous processes and inserting a spinal needle at the midline. Then, a first skin mark corresponding to a posterior limit of the facet joints of the spinous processes of vertebrae 204, 206 may be made, followed by a second skin mark substantially perpendicular to the first mark. The second skin mark is drawn from the first skin mark until the second skin mark intersects the spinal needle. The surgeon may then make the incision about 1 centimeter posterior to the first skin mark. Advantageously, the procedure described herein may be performed through an incision less than 2.6 centimeters, leading to less blood loss, improvements in recovery time and hospital stay, and less scarring than traditional open surgeries.

After making the incision, a guidewire may be introduced into the patient's body, which may be done using an aiming device under fluoroscopy. To access the intervertebral disc space 102, the surgeon may use the access point of Kambin's triangle 100 such that the guidewire traverses between exiting root nerve 106, superior endplate vertebra 108, and traversing root nerve 110. An anterior trajectory may be used. The surgeon may insert the guidewire through the incision and into the intervertebral disc space 102 to guide the placement of interbody cage 202 and other instrumentation. Once the guidewire has reached or pierced the intervertebral disc space 102, the aiming device may be removed. One or more dilators may then be advanced along the guidewire as necessary to dilate the surrounding muscles and tissues, followed by advancing one or more sleeves to facilitate insertion of the interbody cage 202. Each subsequent dilator may have a larger diameter than the previous dilator. Similarly, each subsequent sleeve may have a larger diameter than the previous sleeve. Once the final sleeve has been advanced to intervertebral disc space 102, the smaller sleeves and dilators may be removed from the patient. In some embodiments, the guidewire is also removed from the patient, leaving a single sleeve in place through which interbody cage 202 may be inserted. In some embodiments, the interbody cage 202 comprises a bore 212 therethrough such that interbody cage 202 may be advanced along the guidewire and into the disc space.

In some embodiments, at least a portion of the intervertebral disc 104 is removed prior to insertion of interbody cage 202. For example, a microdiscectomy may be performed through the sleeve. In some embodiments, the nucleus pulposus 214 may be removed and replaced with bone graft 208 prior to inserting the interbody cage 202 into intervertebral disc space 102. Similarly, in some embodiments, at least a portion of the anulus fibrosus 216, which surrounds the nucleus pulposus 214, may be removed from intervertebral disc space 102. For example, as illustrated in FIG. 2B, all of the nucleus pulposus 214 has been removed from intervertebral disc space 102 and is being replaced with bone graft 208. Additionally, a portion of nucleus pulposus 214 has been removed to allow for insertion of interbody cage 202 and removal of vertebrae 204. In some embodiments, electrophysiological monitoring is used during the operation to ensure contact with the root nerve 106 is avoided.

Figure 2C:
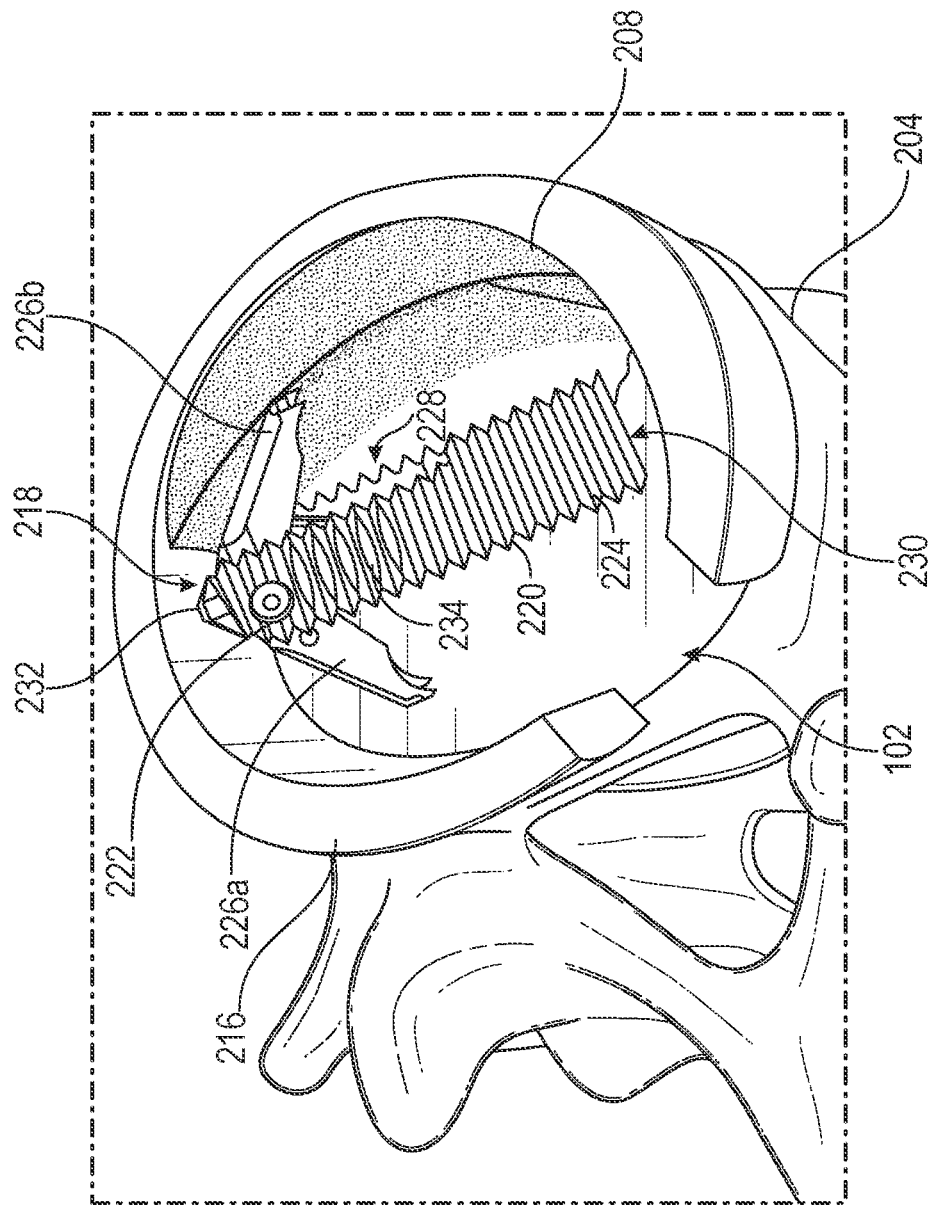
FIG. 2C illustrates a second embodiment of an interbody cage with extendable wings to provide stabilization in the intervertebral disc space for some embodiments.

FIG. 2C illustrates a second embodiment of an interbody cage 218 for some embodiments of the present disclosure. Interbody cage 218 may be substantially similar to the below-described interspinous-interlaminar implant 1000.

Interbody cage 218 may comprise a main body 220, comprising a distal end 222 and a proximal end 224. An extendable first wing 226b and an extendable second wing 226b may be located on distal end 222. Wings 226a, 226b may form a distal anchor of interbody cage 218. In some embodiments, wings 226a, 226b extend out of a substantially rectangular window 228 in main body 220. Each wing 226a, 226b may anchor between the vertebrae 204, 206. By anchoring between vertebrae 204, 206 with wings 226a, 226b, stability of vertebrae 204, 206 is improved. Specifically, the winged design of interbody cage 218 may improve the rotational stability of vertebrae 204, 206. In some embodiments, interbody cage 218 comprises a second pair of wings on the proximal end 224. In some embodiments, proximal end 224 comprises bore 230 configured to receive an insertion instrument (described below) used to insert interbody cage 218.

Distal end 222 of main body 220 may include a conical distal tip 232 having a rounded or a sharp, pointed distalmost end. In some embodiments, interbody cage 218 includes helical threads on an exterior surface thereof. In some embodiments, main body 220 may alternatively, or additionally, include cutting threads or box threads. The helical threads may be provided along the entire exterior surface of main body 220 or along only a portion of the exterior surface of main body 220. In some embodiments, distal end 222 has a smooth exterior surface without any threads thereon. In some embodiments, distal end 222 comprises a solid tip for providing strength during insertion of interbody cage 218. In some embodiments, the external threading on main body 220 further comprises flats 234. In some embodiments, two sets of flats 234 are provided and spaced about 180 degrees apart on main body 220. In some embodiments, the flats 234 are spaced about 90 degrees apart from the wings 226a, 226b. In some embodiments, interbody cage 218 is inserted into intervertebral space 102 such that one set of the flats 234 contacts vertebrae 204, and the other set of flats 234 contacts vertebrae 206, which may further improve the rotational stability of vertebrae 204, 206. Flats 234 may also aid in sliding the interbody cage 218 through the interspinous space during final tightening with an insertion device (discussed below).

Interbody cage 218 may further comprise first wing 226a and second wing 226b. Wings 226a, 226b may be deployable between a closed position (see wings 3000a, 3000b of implant 1000 illustrated in FIG. 3A) and an open position as shown (see also FIGS. 3B and 5A-5B). When interbody cage 218 is inserted into the patient (e.g., through Kambin's triangle 100) and into intervertebral disc space 102, wings 226a, 226b may be maintained in the closed position. Interbody cage 218 may be inserted through intervertebral disc space 102 until interbody cage 218 is fully engaged between vertebrae 204, 206 such that the wings 226a, 226b can be deployed therebetween to provide rotational stability. In some embodiments, wings 226a, 226b have fangs or teeth for engaging with vertebrae 204, 206. In some embodiments, a single interbody cage 218 is inserted into intervertebral disc space 102. In other embodiments multiple (e.g., two) interbody cage 218 may be inserted between vertebrae 204, 206.

Advantageously, by performing the anterior fusion and the posterior fusion through the same incision, the surgeon may utilize the same sleeves and dilators to prepare the intervertebral disc space 102 for the anterior fusion and the interspinous or interlaminar space for the posterior fusion. In some embodiments, the same guidewire is used for both procedures. The surgeon may reposition the guidewire and change the trajectory, from the anterior trajectory and to a posterior trajectory, to access the interspinous space for posterior fusion, as discussed below. The dilators and sleeves may be reinserted and/or repositioned as necessary to prepare the interspinous or interlaminar space for insertion of the spinal fusion implant.

Surgical Techniques

Various surgical techniques may be used for accessing vertebrae 204, 206 and inserting interbody cage 202, 218 into intervertebral disc space 102. In some embodiments, the below-described techniques are used to access intervertebral disc space 102 via Kambin's triangle 100. In some embodiments, the below-described techniques provided access to intervertebral disc space 102 without going through Kambin's triangle 100.

In some embodiments, a posterior lateral interbody fusion (PLIF) technique is used to access the spine. For PLIF, the patient is in the prone position such that the surgeon can access their spine posteriorly, and an incision is made on the patient's back. The surgeon may remove a portion of the patient's lamina to access intervertebral disc space 102. As described above, part of nucleus pulposus 214 and/or anulus fibrosus 216 may also be removed to provide an opening for inserting interbody cage 202, 218 therein. If necessary, one or both of vertebrae 204, 206 may be repositioned to restore the vertebrae 204, 206 to its proper position.

In some embodiments, an anterior lateral interbody fusion (ALIF) technique is used to access the spine. For ALIF, the patient is positioned supine such that the surgeon can access their spine anteriorly, and an incision is made on a patient's stomach. The incision may be between about 3 centimeters and about 5 centimeters in length. The patient's abdominal muscles and blood vessels may be moved and/or retracted to access the vertebrae. The vertebrae 204, 206 may then be repositioned as necessary, and portions of nucleus pulposus 214 and anulus fibrosus 216 may be removed to provide access for inserting interbody cage 202, 218.

In some embodiments, a transforaminal lateral interbody fusion (TLIF) technique may be used to access the spine. For TLIF, the patient is in the prone position such that the surgeon can access their spine posteriorly, and an incision is made on the patient's back. Portions of vertebrae 204, 206 may be removed to provide access to intervertebral disc space 102, and portions of nucleus pulposus 214 and anulus fibrosus 216 may also be removed for insertion of interbody cage 202, 218.

In some embodiments, an oblique lateral interbody fusion (OLIF) technique is used to access the spine. The patient is positioned in the lateral decubitus position with the approach side facing up, and a transverse incision is made, and the abdominal wall muscles, psoas muscle, and surrounding vessels are manipulated to provide access to the spine. The anterolateral portion of intervertebral disc space 102 is exposed and an interbody cage 202, 218 inserted therein.

In some embodiments, an extreme lateral interbody fusion (XLIF) technique is used to access the spine. The patient is positioned in the lateral decubitus position with the approach side facing up. An incision is made on the patient's side. The abdominal muscles are split to provide access to the spine, and nucleus pulposus 214 and anulus fibrosus 216 are at least partially removed to provide access to intervertebral disc space 102 for insertion of interbody cage 202, 218 therein.

As is known to those skilled in the art, each of the above-described techniques may include the use of dilators, sleeves, and other instrumentation (discussed below) as necessary to dilate, distract, decorticate, retract and otherwise prepare the target space for insertion of a cage.

Posterior Fusion and Implant

Figure 3A:
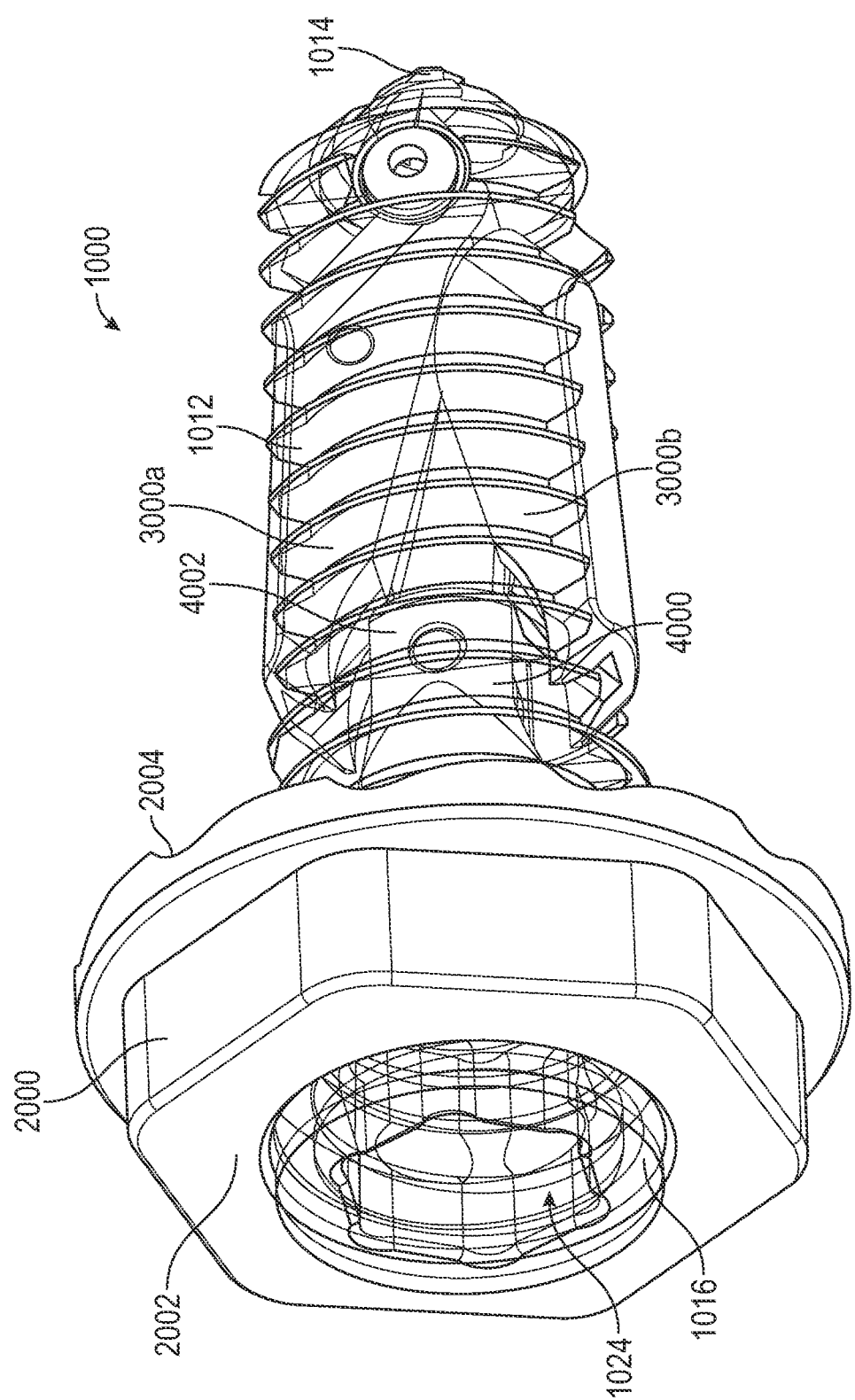
FIG. 3A illustrates an interspinous-interlaminar implant for posterior fusion for some embodiments.
Figure 3B:
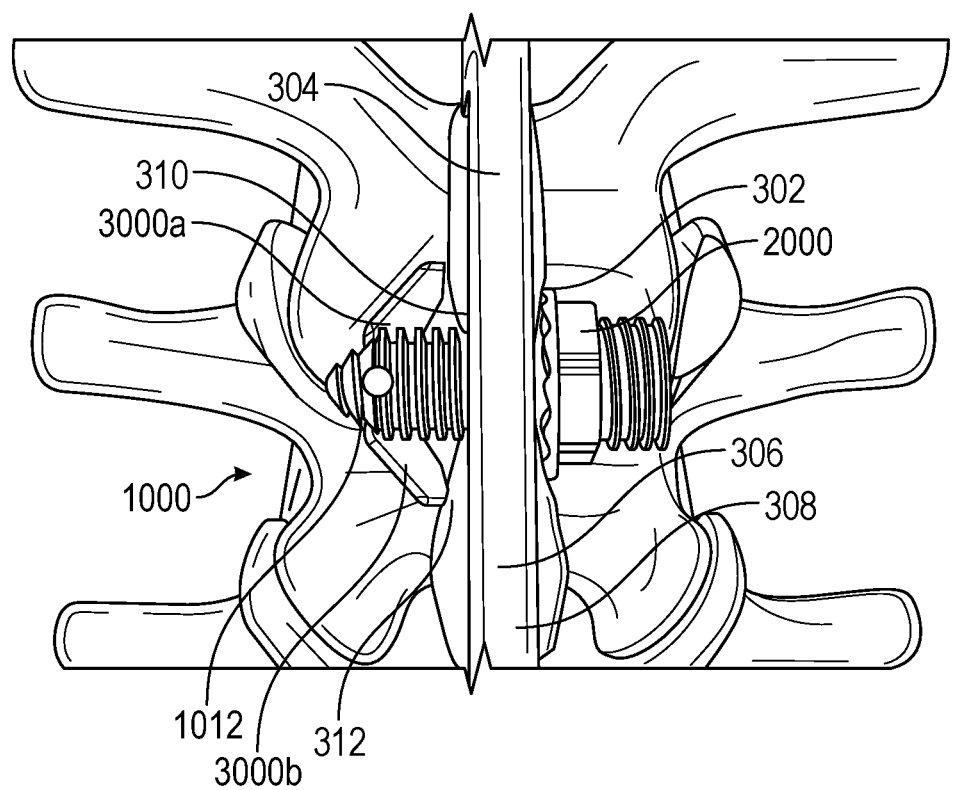
FIG. 3B illustrates the interspinous-interlaminar implant inserted into an interspinous space of the spine for some embodiments.

An exemplary embodiment of an implant 1000 for interspinous-interlaminar fusion with partial features shown and described for the sake of brevity is illustrated in FIGS. 3A and 3B. Further details can be found in application Ser. No. 17/677,677, incorporated by reference herein in its entirety. Implant 1000 is intended for plate fixation/attachment to the spinous process or lamina for achieving fusion for lumbar spinal stenosis, degenerative disc disease, spondylolisthesis, trauma, and/or tumors. Implant 1000 may be inserted via a minimally invasive lateral approach (L1-S1) or a minimally invasive posterior approach (T1-S1). Beneficially, implant 1000 may be percutaneously placed, providing stabilization of the spine, can be used with bone graft material to promote fusion, requires less than a 2.6 cm incision, and can be inserted with local or general anesthesia. As such, the recovery time may be relatively quicker for the patient and the hospital stay may likewise be relatively shorter.

FIG. 3A illustrates implant 1000 in a closed configuration. In some embodiments, implant 1000 includes a main body 1012, comprising a distal end 1014 and a proximal end 1016. Implant 1000 further includes a nut 2000 located on the proximal end 1016 of main body 1012 and extendable first and second wings 3000a, 3000b on the distal end 1014 of main body 1012. Wings 3000a, 3000b may form a distal anchor of implant 1000, and nut 2000 may form a proximal anchor of implant 1000 for anchoring implant 1000 in bone.

Distal end 1014 of main body 1012 may include a conical distal tip having a rounded distalmost end. In some embodiments, the conical distal tip has a sharp, pointed distalmost end. In some embodiments, main body 1012 includes helical threads on an exterior surface thereof. In some embodiments, main body 1012 may alternatively, or additionally, include cutting threads or box threads. The helical threads may be provided along the entire exterior surface of 1012 or along only a portion of the exterior surface of main body 1012. In some embodiments, distal end 1014 includes cutting threads to aid in inserting implant 1000 into bone. In some embodiments, distal end 1014 has a smooth exterior surface without any threads thereon. In some embodiments, distal end 1014 comprises a solid tip for providing strength during insertion of the implant 1000. In some embodiments, implant 1000 comprises flats 234. In some embodiments, flats 234 are in-line with wings 3000a, 3000b.

Nut 2000 may be provided on the proximal end 1016 of main body 1012. In some embodiments, nut 2000 has a proximal side 2002, a distal side 2004, and an internal bore therethrough. In some embodiments, the internal bore has internal helical threads for cooperating with helical threads on the exterior surface of main body 1012. In operation, the nut 2000 can be rotated (e.g., via an insertion instrument, described below) to move the nut 2000 longitudinally along the shaft of main body 1012 such that the distal side 2004 engages tissue and/or bone. In some embodiments, distal side 2004 forms a grip plate having a textured surface. The textured surface may be configured to engage bone or tissue when the implant 1000 is placed in the body to help anchor implant 1000 in place. In some embodiments, nut 2000 is provided in two sizes—a first size for implants of 8 mm, 10 mm, and 12 mm; and a second size for implants of 14 mm and 16 mm.

Figure 5A:
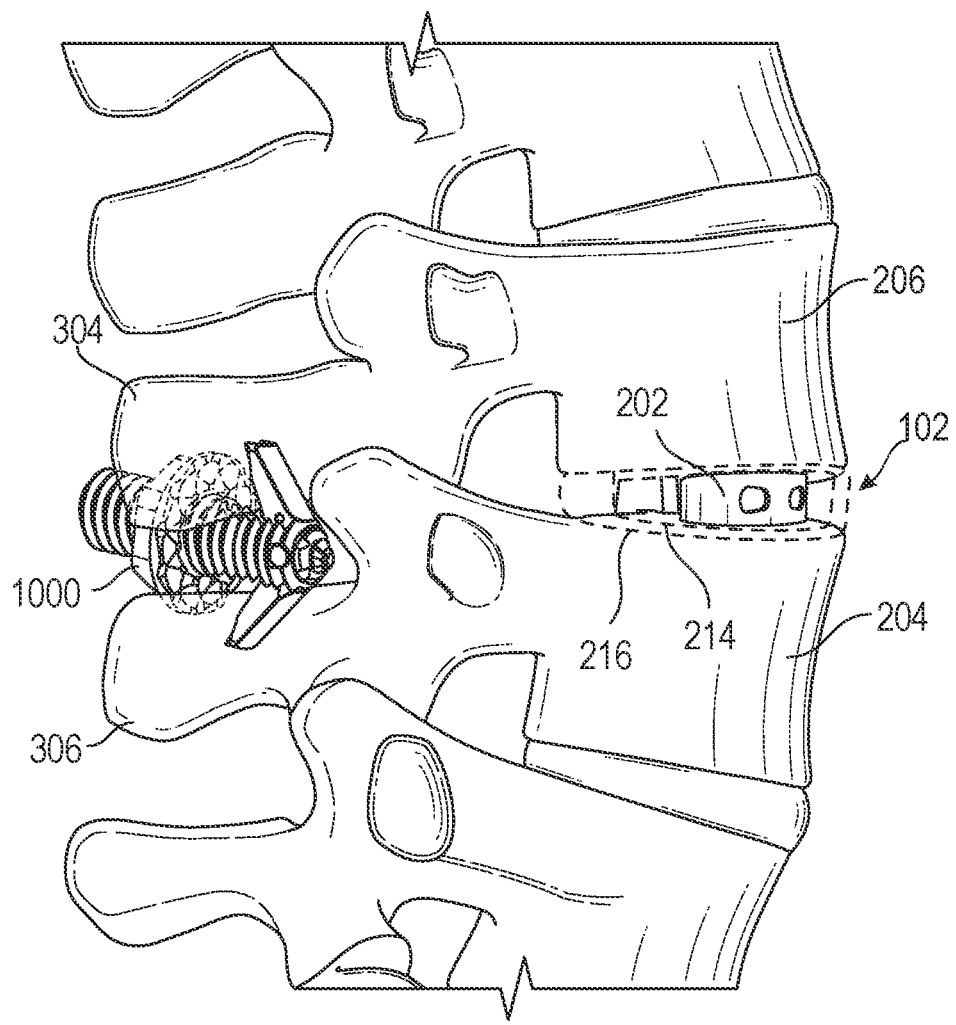
FIG. 5A illustrates the spine with the interbody cage and the interspinous-interlaminar implant inserted therein resulting from the single incision anterior and posterior fusion spinal procedure for some embodiments.
Figure 5B:
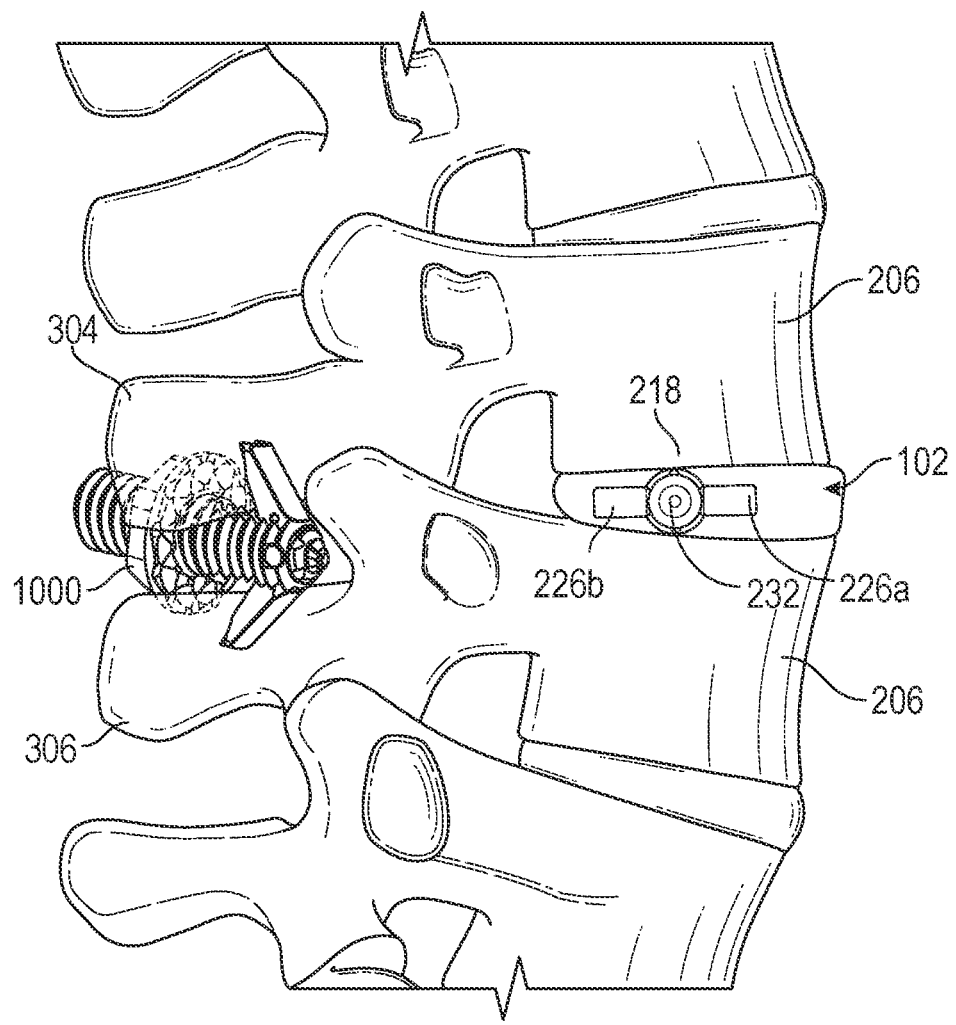
FIG. 5B illustrates the spine with the second embodiment of the interbody cage and the interspinous-interlaminar implant inserted therein resulting from the single incision anterior and posterior fusion spinal procedure for some embodiments.

Implant 1000 may further comprise a first wing 3000a and a second wing 3000b. Wings 3000a, 3000b may be deployable between a closed position (FIG. 3A) and an open position (FIGS. 3B and 5A-5B). When implant 1000 is inserted into the patient through the interspinous ligament, wings 3000a, 3000b may be maintained in the closed position. Once implant 1000 is in the desired implantation space, wings 3000a, 3000b may be deployed with the insertion instrument and engage with bone to anchor implant 1000 at the target process space, as discussed further below. In some embodiments, implant 1000 comprises a pair of proximal wings on proximal end 1016.

In some embodiments, all, or part, of implant 1000 and/or interbody cage 218 may be composed of titanium or a titanium alloy. In some embodiments, all, or part of, implant 1000 and/or interbody cage 218 may be composed of stainless steel. In some embodiments, all, or part of, implant 1000 and/or interbody cage 218 may be composed of a polymer or a bioabsorbable material. In some embodiments, an outer surface of implant 1000 and/or interbody cage 218 is coated with hydroxyapatite (HA). As described above, interbody cage 218 may be substantially similar to implant 1000. Differing from implant 1000, in some embodiments, interbody cage 218 does not comprise a nut on proximal end 222.

The posterior fusion procedure for inserting implant 1000 between adjacent spinous processes may proceed as follows. The patient may remain in the same prone position described above for the anterior fusion procedure. If not already tilted, the surgeon may tilt the pelvis by inclining the surgical table at the level of the pelvis, allowing for natural distraction of the spinous processes. When inserting implant 1000 after insertion of the interbody cage 202, 218 through Kambin's triangle 100, the guidewire may be repositioned from the intervertebral disc space 102 and advanced between the spinous processes to pierce the interspinous ligament. Alternatively, or additionally, a second guidewire may be used and advanced between the spinous processes to pierce the interspinous ligament. As described above, an aiming device may be used to aid the surgeon inserting the guidewire into the interspinous process space. Once the guidewire is advanced as desired, which may be approximately 2 cm across the midline of the spine, the aiming device may be removed with the guidewire remaining in place. A guidewire extension may be placed on a proximal end of the guidewire to help maintain guidewire placement during the procedure. A series of dilators may then be placed over the guidewire to create a pathway to the spinous processes. The dilators may be the same dilators used to dilate intervertebral disc space 102. One or more sleeves may be advanced to dock against the ipsilateral aspect of the spinous processes. In some embodiments, the one or more sleeves are the same sleeves used in the anterior interbody procedure.

A graduated bone tap may then be inserted over the guidewire. The bone tap may be used to distract the spinous processes and partially decorticate the spinous processes for stimulating bone growth. The bone tap may be rotated clockwise to gradually decorticate and/or to distract the spinous processes. The bone tap may be threaded into the interspinous process space such that the threads are engaged with the spinous processes and tap a path for implant 1000 to be inserted along. Once adequate distraction is obtained, the degree of distraction can be determined by viewing a sizing hole on a distal end of the bone tap under fluoroscopy. In some embodiments, the bone tap comprises multiple sizing holes on a distal end thereof, and the sizing hole that is located between the spinous processes indicates the size of the implant to be used. This degree of distraction thereby determines the appropriate size of implant 1000, which may be a 6 mm, 8 mm, 10 mm, 12 mm, 14 mm, 16 mm, or 18 mm implant. Other implant sizes may be used without departing from the scope hereof. The bone tap and the guidewire can then be removed, and the spinal implant 1000 can be placed. Before implant 1000 is inserted into the patient, bone graft 208 may be added. Specifically, bone graft 208 may be added by opening wings 3000a, 3000b and adding bone graft 208 into a lumen of the main body 1012. Bone graft 208 may also be applied around the exterior threads of implant 1000.

In some embodiments, implant 1000 is configured for insertion into the interlaminar space. The implantation into the interlaminar space may be substantially similar to the above-described method of inserting implant 1000 into the interspinous space. The guidewire may be advanced under fluoroscopy to the target interlaminar space. Dilators and sleeves may be sequentially advanced over the guidewire as needed to distract surrounding muscle and tissue. Thereafter, the bone tap may be inserted to tap a path for implant 1000. Finally, implant 1000 may be inserted through the sleeve and into the interlaminar space. In some embodiments, a facet rasp is used to remove portions of the facet joints. In some embodiments, portions of the laminae are also removed to facilitate insertion of implant 1000.

In some embodiments, implant 1000 and/or interbody cage 202, 218 can be inserted using any of the above-described surgical techniques or any other surgical technique for accessing the spine now known or later developed.

Implant 1000 may be inserted with an insertion instrument which may be reusable or disposable. Exemplary insertion instruments are disclosed in commonly-assigned U.S. Pat. No. 10,420,591, U.S. Patent Application Publication No. 2020/0015864, and U.S. application Ser. No. 17/716,833, which are hereby incorporated by reference in their entirety. The insertion instrument may be rotatable to rotate implant 1000, thereby self-threading implant 1000 through the interspinous process or interlaminar space. Rotation of implant 1000 through the target space provides further distraction thereof, which may tighten and lock implant 1000 in position. Once in the target treatment space, the insertion instrument may be configured to deploy wings 3000a, 3000b. For example, the insertion instrument may comprise a plunger assembly which, when actuated, causes deployment of wings 3000a, 3000b. In some embodiments, the plunger assembly comprises a plunger shaft which engages an implant plunger 4000 of implant 1000. The implant plunger 4000 may comprise a proximal end 4002, a distal end, and a central bore. Implant plunger 4000 may be connected at the distal end to a first linkage and a second linkage. The first linkage may be connected to the first wing 3000a, and the second linkage may be connected to the second wing 3000b. The central bore of the implant plunger 4000 may receive the plunger shaft through a bore 1024 of main body 1012. Implant plunger 4000 may be moved longitudinally within bore 1024, via the insertion instrument, which actuates the first linkage and the second linkage to open and close wings 3000a, 3000b. Distal longitudinal movement of implant plunger 4000 may actuate wings 3000a, 3000b to an open configuration, and proximal longitudinal movement of implant plunger 4000 may actuate wings to return to the closed configuration. Therefore, implant 1000 may be easily repositioned and/or removed from the patient by actuating implant 1000 between the open and the closed configurations. In some embodiments, bore 228 on interbody cage 218 is substantially similar to bore 1024 on implant 1000.

Likewise, the above-described insertion instrument (or another similar tool) may be used to insert interbody cage 218 into intervertebral disc space 102 (via Kambin's triangle 100 in some embodiments). The insertion instrument may couple to interbody cage 218 via implant body bore 230 and rotate interbody cage 218 to the target location. The insertion instrument may then be used to deploy wings 226a, 226b via the plunger assembly. Interbody cage 218 may comprise an implant plunger (not shown) as described above with respect to implant 1000, and the implant plunger may be actuated to deploy wings 226a, 226b.

FIG. 3B illustrates implant 1000 in place in the interspinous process space. Nut 2000 may engage a first lateral surface 302 of a first spinous process 304 and a second lateral surface 306 of a second spinous process 308, thereby forming a proximal anchor. Wings 3000a, 3000b may dock against a third opposite surface 310 of first spinous process 304 and a fourth opposite surface 312 of second spinous process 308, thereby forming a distal anchor. In some embodiments, wings 3000a, 3000b comprise fangs for engaging third opposite surface 310 and fourth opposite surface 312. As described above, bone graft 208 may be added to implant 1000 before insertion to promote bony fusion between spinous processes 304, 308. Thus, in concert with cage 202, implant 1000 may help to stabilize damaged vertebra. By utilizing the access point of Kambin's triangle 100, cage 202, and implant 1000, both posterior and anterior fusion may be achieved without having to reposition the patient during the operation.

Single Incision Anterior and Posterior Fusion Procedure

Figure 4:
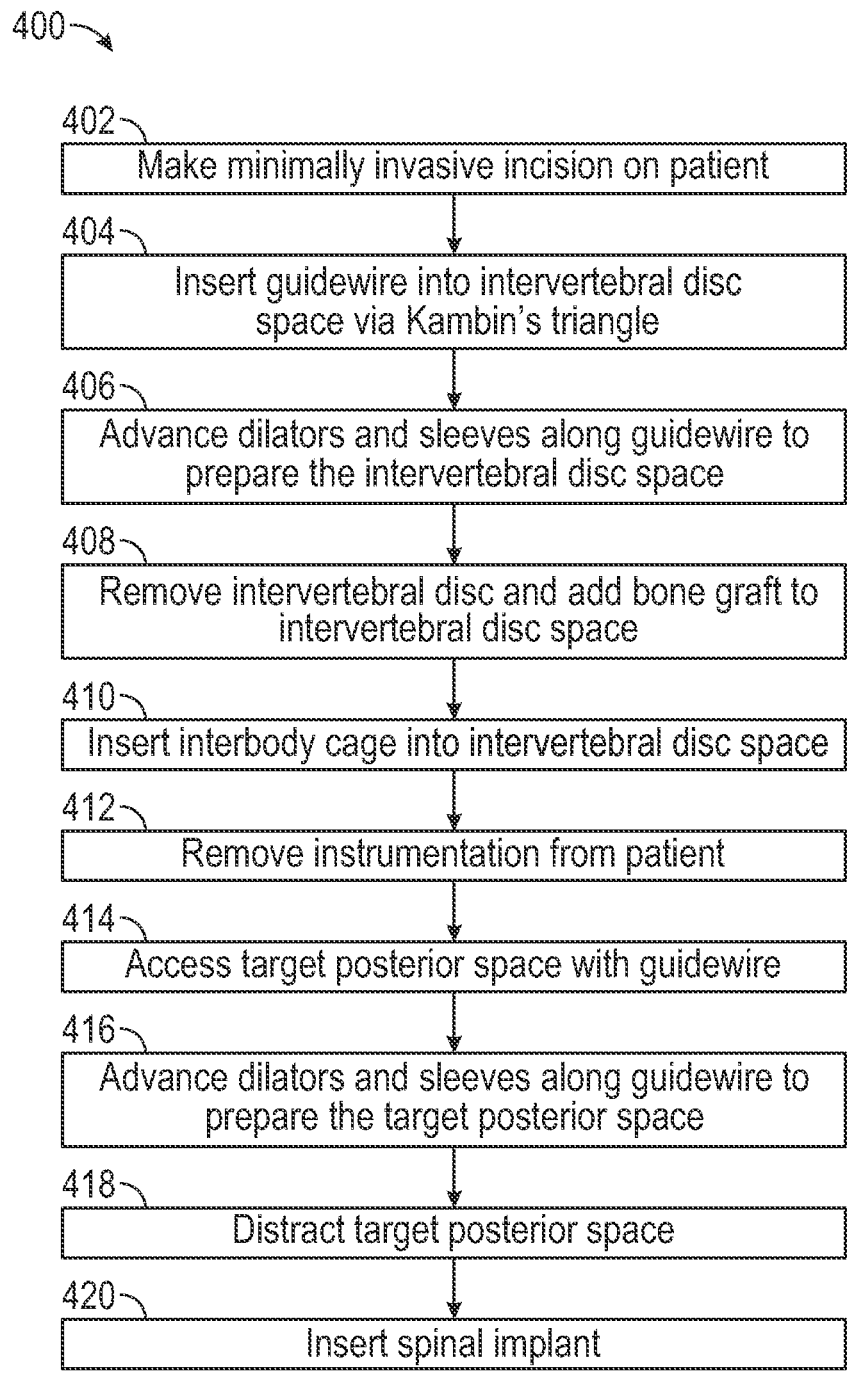
FIG. 4 illustrates a method for a single incision anterior and posterior fusion spinal procedure for some embodiments.

FIG. 4 illustrates an exemplary method 400 for a single incision anterior and posterior fusion spinal procedure for some embodiments. The anterior interbody fusion and the posterior fusion may be performed through a single percutaneous lateral incision made on a patient as described above. The operation may be performed with the patient lying posteriorly on their stomach in a prone position or lying on their side in the lateral decubitus position. The operation may be performed under AP fluoroscopy to provide internal imaging of the spine.

At step 402, an incision may be made on the patient to provide access to the spine. The incision may be made on either lateral side of the spine. The incision may be minimally invasive, having a length of less than about 2.6 centimeters. As previously discussed, it is advantageous to perform both the anterior and the posterior fusion procedures through the same minimally invasive incision to minimize recovery time, hospital stay, scarring, and the like.

The anterior interbody fusion procedure through Kambin's triangle 100 with an interbody cage 202, 218 may be performed first. At step 404, a guidewire may be inserted through the incision to guide the surgeon in locating the intervertebral disc space 102. The access point of Kambin's triangle 100 may be used to operate in intervertebral disc space 102. Utilizing Kambin's triangle 100 may substantially reduce the risk of the surgeon damaging critical spinal structures (e.g., vascular, neural) during operation, as these critical spinal structures are not present in the area defined by Kambin's triangle 100. Furthermore, Kambin's triangle 100 allows intervertebral disc space 102 to be accessed from a percutaneous lateral incision such that both anterior and posterior fusion may be performed via the same percutaneous lateral incision. As described above, electrophysiological monitoring may be used to ensure contact with the root nerve is avoided during the procedure.

Next, at step 406, dilators and sleeves may be advanced along the guidewire to the intervertebral disc space 102 to prepare intervertebral disc space 102 for insertion of interbody cage 202, 218. One or more dilators may be placed over the guidewire, with each subsequent dilator having a larger diameter than the previous dilator to dilate the surrounding muscle and tissue. The one or more dilators may be advanced and abut vertebrae 204, 206. In some embodiments, the one or more dilators are partially inserted into the intervertebral disc space 102. One or more sleeves may then be advanced over the one or more dilators and dock against vertebrae 204, 206 to facilitate insertion of interbody cage 202, 218 therethrough. After insertion of the one or more sleeves, the one or more dilators along with any smaller sleeves may be removed, leaving the one largest sleeve docked against vertebrae 204, 206. In some embodiments, distraction of the intervertebral space 102 is also performed. Distraction may be done with a tool and/or via the insertion of interbody cage 218 itself.

Next, at step 408, some, or all, of the intervertebral disc 104 may be removed from intervertebral disc space 102. The intervertebral disc 104 may be removed to provide space for interbody cage 202 to be inserted into intervertebral disc space 102. For example, portions of the anulus fibrosus 216 may be removed from the intervertebral disc space 102 to provide access to insert the interbody cage 202 into intervertebral disc space 102. In some embodiments, a first portion of the anulus fibrosus 216 is removed to provide an opening for insertion cage 218 and a second portion of the anulus fibrosus 216, which may be substantially opposite the first portion, is removed to provide an exit through which distal end 222 of interbody cage 218 can be extended for deploying wings 226a, 226b. A microdiscectomy may be performed through a sleeve to remove the intervertebral disc 104. In some embodiments, the removed disc is at least partially replaced with bone graft 208. For example, bone graft 208 may be added to intervertebral disc space 102 to substantially fill intervertebral disc space 102, while leaving sufficient room for the insertion of interbody cage 202, 218. One or more interbody cages 202, 218 may be inserted into intervertebral disc space 102.

At step 410, one or more interbody cages 202, 218 may be inserted into the intervertebral disc space 102. Insertion of interbody cage 202, 218 may aid in decompressing the spine. In some embodiments, the interbody cage 202, 218 is inserted through the sleeve using an insertion instrument. In some embodiments, interbody cage 202, 218 is inserted along the guidewire (which may be disposed within the sleeve) and into the intervertebral disc space 102. When interbody cage 218 is used, distal end 222 may be inserted through intervertebral disc space 102 to deploy wings 226a, 226b and engage the wings with vertebrae 204, 206. In some embodiments, bone graft 208 is added to the interior and/or exterior of interbody cage 202, 218. Thus, bony fusion between vertebrae 204, 206 may be promoted.

Thereafter, at step 412, instrumentation for the anterior interbody fusion procedure may be removed from the patient. The instrumentation may comprise the above-described guidewire, dilators, sleeves, electrophysiological monitoring, and any other surgical tools used during the procedure. In some embodiments, at least one of the guidewire or the sleeve is left within the patient, and the surgeon may adjust the trajectory of the instrumentation to access the target posterior space (i.e., interspinous or interlaminar) for the posterior fusion procedure.

The posterior fusion procedure may then be performed. If not already inclined, the surgeon may incline the surgical table at the level of the pedicle to allow for natural distraction of the spinous processes.

At step 414, the surgeon may utilize the guidewire to locate the target process space. As discussed above, the guidewire may pierce the interspinous ligament, and the surgeon may use an aiming device to insert the guidewire under fluoroscopy. When performing interlaminar fusion, the guidewire may pierce the interspinous ligament connecting first vertebra 204 to second vertebra 206.

At step 416, dilators and sleeves may be advanced along the guidewire to prepare the target space. Step 416 may be substantially similar to step 406 described above. The dilators and sleeves may dock against the lateral aspect of the spinous processes. For interlaminar fusion, the dilators and sleeves may dock against the lamina of first vertebra 204 and second vertebra 206. After the one or more sleeves are docked against the lateral aspect of the spinous processes, the dilators and smaller sleeves may be removed from the patient, leaving the largest sleeve and guidewire in place.

Next, at step 418, distraction of the target posterior space may be performed with a graduated bone tap. The bone tap may be inserted through the sleeve. The distraction may decorticate the spinous processes. An insertion length of the bone tap/distractor into the interspinous process space may be used to determine a size of the implant 1000 as described above. Thereafter, the guidewire may be removed. Lastly, at step 420, an insertion instrument may be used to insert the fusion device into the interspinous or interlaminar space. Wings 3000a, 3000b of the implant 1000 may be deployed and engage the contralateral aspect of the spinous processes to secure implant 1000 to the spine. Alternatively, when inserting implant 1000 into the interlaminar space, wings 3000a, 3000b may engage with the laminae. As previously described, implant 1000 may be filled with bone graft 208 to promote fusion between the adjacent spinous processes.

In some embodiments, the above-described method 400 may be provided as instructions with a surgical kit. For example, the surgical kit may comprise the instrumentation required to perform the surgery, such as one or more interbody cages 202,218, implant 1000, the guidewire, the dilators, the sleeves, an insertion instrument, or any combination thereof. The surgical kit may provide multiple sizes of the tools and/or implants/cages which may be selected based on the size of the patient. The surgeon may use the surgical kit to perform the anterior and posterior fusions and follow the above-described method to carry out the operations.

It will be appreciated that the posterior interspinous-interlaminar fusion procedure may be performed prior to performing the anterior interbody fusion. That is, in some such embodiments, steps 404-410 may be performed prior to steps 414-420 without departing from the scope hereof. It may be advantageous to perform the posterior fusion prior to the anterior fusion if performing the posterior fusion results in distracting the intervertebral space for the anterior fusion. Likewise, if anterior fusion causes distraction of the space for posterior fusion, performing the anterior fusion before the posterior fusion may be advantageous.

FIG. 5A illustrates interbody cage 202 and implant 1000 inserted into the spine of a patient as a result of the above-described single incision anterior and posterior fusion procedure for some embodiments. As illustrated in FIG. 5A and described above, insertion of interbody cage 202 into intervertebral disc space 102 and implant 1000 into the interspinous process space allows for bony fusion to occur at both the anterior and the posterior spine. One or more interbody cage 202 may be inserted into intervertebral disc space 102.

FIG. 5B illustrates interbody cage 218 and implant 1000 inserted into the spine of a patient as a result of the above-described single incision anterior and posterior fusion procedure for some embodiments. As shown, wings 226a, 226b are engaged with vertebrae 204, 206, and flats 234 are in contact with the vertebrae 204, 206. The use of wings 226a, wings 226b provides additional rotational stability between vertebrae 204, 206. The increased rotational stability can also help prevent movement of interbody cage 218 in intervertebral disc space 102. One or more interbody cages 218 may be inserted into intervertebral disc space 102. By performing both the anterior fusion procedure and the posterior fusion procedure through the same incision, recovery time and hospital stay may be decreased, among other benefits described herein. Furthermore, operation time may be reduced as the patient can remain in a singular position throughout the entire operation.

It will be appreciated that embodiments herein are not limited to a single incision procedure for inserting a spinal implant and an interbody cage through the single incision. In some embodiments, two or more incisions may be made to provide two or more access points for inserting medical implants into the patient. For example, a first incision may be made to access intervertebral disc space 102 via Kambin's triangle 100 for insertion of an interbody cage 202, 218, and a second incision made to access the interspinous processes for insertion of implant 1000. Likewise, when inserting implant 1000 using ALIF, PLIF, TLIF, XLIF, OLIF, or other surgical techniques, a separate incision may be made for inserting interbody cage 202, 218 via Kambin's triangle 100.

Many different arrangements of the various components depicted, as well as components not shown, are possible without departing from the scope of the claims below. Embodiments of the present disclosure have been described with the intent to be illustrative rather than restrictive. Alternative embodiments will become apparent to readers of this disclosure after and because of reading it. Alternative means of implementing the aforementioned can be completed without departing from the scope of the claims below. Certain features and sub-combinations are of utility and may be employed without reference to other features and sub-combinations and are contemplated within the scope of the claims. Although the present disclosure has been described with reference to the embodiments illustrated in the attached drawing figures, it is noted that equivalents may be employed, and substitutions made herein, without departing from the scope of the present disclosure as recited in the claims.

The invention claimed is:

1. A method for a single incision anterior fusion and posterior fusion spinal procedure, the method comprising:
   providing instructions for performing the single incision anterior fusion and posterior fusion spinal procedure, the instructions comprising:
   make a minimally invasive incision on a patient to provide percutaneous lateral access to a spine of the patient;

advance a guidewire through the minimally invasive incision and into an intervertebral disc space located between a first vertebra and a second vertebra of the spine;

advance at least one dilator through the minimally invasive incision and over the guidewire to dilate the intervertebral disc space;

advance at least one sleeve through the minimally invasive incision and over the at least one dilator;

insert, via an anterior trajectory and through an access point defined by Kambin's triangle, an interbody cage into the intervertebral disc space, wherein the interbody cage comprises a first wing and a second wing actuatable between an open configuration and a closed configuration, wherein the first wing and the second wing extend laterally out of a window of the interbody cage in the open configuration such that the first wing and the second wing are substantially parallel to the first vertebra and the second vertebra when inserted, and wherein the first wing and the second wing are within the window in the closed configuration;

deploy the first wing and the second wing to transition the interbody cage from the closed configuration to the open configuration;

reposition the guidewire to access a target space between the first vertebra and the second vertebra; and insert, via a posterior trajectory, a spinal fusion implant through the minimally invasive incision and to the target space for stabilization at the target space.

2. The method of claim 1, wherein the target space is an interspinous process space, and wherein the spinal fusion implant is configured to fuse a first spinous process of the first vertebra with a second spinous process of the second vertebra.

3. The method of claim 2, wherein the instructions further comprise:

deploy a first wing and a second wing of the spinal fusion implant, wherein the first wing of the spinal fusion implant is configured to engage with the first spinous process, and the second wing of the spinal fusion implant is configured to engage with the second spinous process wherein the first wing and the second wing of the interbody cage are configured to engage with the first vertebra and the second vertebra when the interbody cage is in the open configuration.

4. The method of claim 2, wherein the instructions further comprise:

distract the first spinous process and the second spinous process with a bone tap.

5. The method of claim 1, wherein the target space is an interlaminar space of the patient, and wherein the spinal fusion implant is configured to fuse a first lamina to a second lamina.

6. The method of claim 1, wherein the interbody cage comprises external threads, the external threads comprising a pair of opposing flats, wherein the pair of opposing flats are located on a surface of the external threads, and wherein the pair of opposing flats are configured to aid in insertion of the interbody cage and provide rotational stability.

7. The method of claim 1, wherein the instructions further comprise:

add bone graft material to at least one of the interbody cage or the spinal fusion implant to promote bony fusion between the first vertebra and the second vertebra.

8. The method of claim 1, wherein the instructions further comprise:

prior to inserting the interbody cage into the intervertebral disc space, remove at least a portion of an intervertebral disc disposed in the intervertebral disc space; and replace the portion of the intervertebral disc with bone graft.

9. The method of claim 1, wherein the single incision anterior fusion and posterior fusion procedure is performed in a lumbar spine of the patient.

10. The method of claim 1, wherein the minimally invasive incision comprises a length of less than about 2.6 centimeters.

11. A method for a single incision anterior fusion and posterior fusion spinal procedure, the method comprising:

providing instructions for performing the single incision anterior fusion and posterior fusion spinal procedure, the instructions comprising:

make a minimally invasive incision onto a lateral side of a patient;

access an intervertebral disc space of a spine of the patient using a guidewire;

insert, via an anterior trajectory and through Kambin's triangle, an interbody cage through the minimally invasive incision and into the intervertebral disc space, wherein the interbody cage comprises a first wing and a second wing actuatable between an open configuration and a closed configuration, wherein the first wing and the second wing extend laterally out of a window of the interbody cage in the open configuration such that the first wing and the second wing are substantially parallel to a first vertebra and a second vertebra of the intervertebral disc space, wherein the first wing and the second wing are within the window in the closed configuration, and wherein the first wing and the second wing are deployable and configured to provide rotational stability between vertebrae adjacent to the intervertebral disc space;

deploy the first wing and the second wing, wherein the first wing and the second wing are actuated between the closed configuration and the open configuration;

access an interlaminar space of the spine of the patient using the guidewire;

advance at least one dilator through the minimally invasive incision and over the guidewire to dilate the interlaminar space;

advance at least one sleeve over the at least one dilator;

remove the guidewire from the patient; and insert, via a posterior trajectory, a spinal implant into the interlaminar space.

12. The method of claim 11, wherein the instructions further comprise:

distract the interlaminar space of the spine using a bone tap inserted through the minimally invasive incision and over the guidewire.

13. The method of claim 11, wherein the interbody cage comprises external threads, the external threads comprising a pair of opposing flats, wherein the pair of opposing flats are located on a surface of the external threads, and wherein the pair of opposing flats are configured to aid in insertion of the interbody cage and provide rotational stability.

14. The method of claim 11, wherein the instructions further comprise:

remove at least a portion of an intervertebral disc prior to inserting the interbody cage.

15. The method of claim 11, wherein the instructions further comprise:

remove at least a portion of a facet using a facet rasp to enhance access to the interlaminar space.

16. The method of claim 11, wherein the minimally invasive incision is made on the patient lying in a prone position, and wherein the minimally invasive incision is configured to provide percutaneous lateral access to the spine of the patient.

17. A system for a single incision anterior and posterior spinal fusion procedure, the system comprising:

a guidewire configured for insertion into an incision, wherein the incision is a minimally invasive incision configured to provide percutaneous lateral access to a spine of a patient;

at least one dilator configured to be advanced over the guidewire to dilate the patient;

at least one sleeve configured to be advanced over the at least one dilator;

an interbody cage configured to be inserted through the incision and the at least one sleeve and into an intervertebral disc space, comprising:

a first wing and a second wing, wherein the first wing and the second wing are actuatable between an open configuration and a closed configuration, wherein the first wing and the second wing extend laterally out of a window of the interbody cage in the open configuration such that the first wing and the second wing are substantially parallel to a first vertebra and a second vertebra, wherein the first wing and the second wing are within the window in the closed configuration, and wherein the interbody cage is configured to be inserted through Kambin's triangle and via an anterior trajectory; and a spinal implant configured to be inserted through the incision and across an interspinous process space of the patient, wherein the spinal implant is configured to be inserted via a posterior trajectory.

18. The system of claim 17, wherein the first wing and the second wing are configured to engage with a superior vertebra and an inferior vertebra of the intervertebral disc space when the interbody cage is in the open configuration.

19. The system of claim 18, wherein the interbody cage comprises external threads, the external threads comprising a pair of opposing flats, wherein the pair of opposing flats are located on a surface of the external threads, and wherein the pair of opposing flats are configured to aid in insertion of the interbody cage and provide rotational stability.

20. The system of claim 17, wherein at least one of the interbody cage or the spinal implant is configured to hold bone graft material.

* * * * *